(12) United States Patent
Li et al.

(10) Patent No.: US 12,063,749 B2
(45) Date of Patent: Aug. 13, 2024

(54) METHOD FOR MANUFACTURING MICROELECTRODE FILM

(71) Applicant: BOE TECHNOLOGY GROUP CO., LTD., Beijing (CN)

(72) Inventors: Fan Li, Beijing (CN); Jiangbo Chen, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 729 days.

(21) Appl. No.: 17/264,957

(22) PCT Filed: May 27, 2020

(86) PCT No.: PCT/CN2020/092567
§ 371 (c)(1),
(2) Date: Feb. 1, 2021

(87) PCT Pub. No.: WO2020/238948
PCT Pub. Date: Dec. 3, 2020

(65) Prior Publication Data
US 2021/0315105 A1    Oct. 7, 2021

(30) Foreign Application Priority Data

May 29, 2019 (CN) .......................... 201910458492.1

(51) Int. Cl.
*H05K 3/20* (2006.01)
*A61B 5/263* (2021.01)
(Continued)

(52) U.S. Cl.
CPC ................. *H05K 3/20* (2013.01); *H05K 1/09* (2013.01); *H05K 1/118* (2013.01); *H05K 3/0058* (2013.01);
(Continued)

(58) Field of Classification Search
CPC .............. A61B 2562/125; A61B 5/263; H05K 1/0346; H05K 1/09; H05K 1/118;
(Continued)

(56) References Cited

U.S. PATENT DOCUMENTS

| | | |
|---|---|---|
| 2009/0152109 A1 | 6/2009 | Macpherson |
| 2019/0103532 A1 | 4/2019 | Lee et al. |
| 2021/0315105 A1* | 10/2021 | Li .......................... H05K 3/107 |

FOREIGN PATENT DOCUMENTS

| | | |
|---|---|---|
| CN | 1616708 A | 5/2005 |
| CN | 1772947 A | 5/2006 |

(Continued)

OTHER PUBLICATIONS

Translation of Written Opinion for PCT/CN2020/092567.*
China Patent Office, CN201910458492.1 First Office Action issued on Jul. 5, 2021.

*Primary Examiner* — Sonya M Sengupta
(74) *Attorney, Agent, or Firm* — HOUTTEMAN LAW LLC

(57) ABSTRACT

The present application provides a method for manufacturing a microelectrode film. The method includes: forming at least one recess on the carrier substrate by isotropic etching; forming a microelectrode seed pattern in the recess; growing a microelectrode in the recess by using the microelectrode seed pattern; making a first substrate to be in contact with a side of the carrier substrate having the recess thereon; separating the microelectrode from the carrier substrate to transfer the microelectrode onto the first substrate.

14 Claims, 6 Drawing Sheets

(51) Int. Cl.
*A61N 1/04* (2006.01)
*H05K 1/03* (2006.01)
*H05K 1/09* (2006.01)
*H05K 1/11* (2006.01)
*H05K 3/00* (2006.01)

(52) U.S. Cl.
CPC ......... *A61B 5/263* (2021.01); *A61B 2562/125* (2013.01); *A61N 1/04* (2013.01); *H05K 1/0346* (2013.01); *H05K 3/002* (2013.01); *H05K 2201/0154* (2013.01); *H05K 2201/0323* (2013.01); *H05K 2201/0367* (2013.01); *H05K 2203/0147* (2013.01)

(58) Field of Classification Search
CPC ... H05K 2201/0154; H05K 2201/0323; H05K 2201/0367; H05K 2201/09036; H05K 2203/0147; H05K 2203/308; H05K 3/002; H05K 3/0058; H05K 3/007; H05K 3/107; H05K 3/181; H05K 3/20; A61N 1/04; A61N 1/0476
See application file for complete search history.

(56) References Cited

FOREIGN PATENT DOCUMENTS

| | | |
|---|---|---|
| CN | 1852634 A | 10/2006 |
| CN | 101110355 A | 1/2008 |
| CN | 101149559 A | 3/2008 |
| CN | 101950741 A | 1/2011 |
| CN | 105147280 A | 12/2015 |
| CN | 107622817 A | 1/2018 |
| CN | 107993972 A | 5/2018 |
| CN | 110143569 A | 8/2019 |

\* cited by examiner

METHOD FOR MANUFACTURING MICROELECTRODE FILM

TECHNICAL FIELD

The present application relates to the field of biological electrode technology, in particular to a method for manufacturing a microelectrode film.

BACKGROUND

The microelectrode film generally includes a substrate and a microelectrode(s) disposed on the substrate, the microelectrode being a miniaturized electrode which is an electrode not larger than 200 μm in at least one dimension. Due to the small size, the microelectrode has properties incomparable with the conventional electrode, such as high current density, high response speed, high signal-to-noise ratio and the like. Therefore, it is widely applied to the biological fields of detection, stimulation, and the like of organisms (e.g., tissues, organs of human or animals) increasingly.

The basic principle of adopting a microelectrode film to detect and stimulate an organism is as follows. A microelectrode film is attached to an organism to enable a microelectrode in the microelectrode film to be in contact with the organism, and an electric signal (a voltage) of the organism is acquired by an acquisition device through the microelectrode to realize the detection of the organism; and a stimulation device outputs a stimulation signal (a current) to the organism through the microelectrode to stimulate the organism.

The effective contact area of the microelectrode in the microelectrode film with the organism, that is, an area ratio of a portion of the microelectrode surface which can be in contact with the organism to the microelectrode surface in a case where the microelectrode film is in contact with the organism, has a great influence on the final detection result and the stimulation result, for example, when the stimulation device outputs the same stimulation signal, the larger the area ratio is, the stronger the stimulation signal received by the organism is. Therefore, in order to ensure the accuracy of the final detection and stimulation results, the shape of the microelectrode is preferably adapted to the shape of the organism and the specific application scenes. However, since the shape of an organism varies and application scenes are various, the shape of a microelectrode needs to be various.

SUMMARY

In one aspect, the present disclosure provides a method for manufacturing a microelectrode film, including: forming at least one recess on a carrier substrate by isotropic etching; forming a microelectrode seed pattern in the recess; growing a microelectrode in the recess by using the microelectrode seed pattern; making a first substrate to be in contact with a side of the carrier substrate having the recess thereon; and separating the microelectrode from the carrier substrate to transfer the microelectrode onto the first substrate.

In some embodiments, the microelectrode seed pattern includes boron-doped diamond and the first substrate is a flexible substrate.

In some embodiments, the forming at least one recess on the carrier substrate by isotropic etching includes: forming, on the carrier substrate, a first etching stop layer with an opening by a patterning process, the opening exposing a portion of the carrier substrate; and isotropically etching the portion of the carrier substrate exposed by the opening by using an etchant solution to form the recess on the carrier substrate.

In some embodiments, the isotropically etching the portion of the carrier substrate exposed by the opening by using an etchant solution includes: placing the carrier substrate in the etchant solution, and stirring the etchant solution.

In some embodiments, the isotropically etching the carrier substrate includes: placing the carrier substrate into the etchant solution, and stirring the etchant solution during the etching of the carrier substrate.

In some embodiments, the carrier substrate is a silicon substrate.

In some embodiments, the opening is circular.

In some embodiments, the forming the microelectrode seed pattern in the recess includes: forming a microelectrode seed layer on the side of the carrier substrate having the recess thereon, and removing a portion of the microelectrode seed layer outside the recess by etching.

In some embodiments, after growing the microelectrode in the recess by using the microelectrode seed pattern and before making the first substrate to be in contact with the side of the carrier substrate having the recess thereon, the method further includes: forming at least one lead connected with the microelectrode on the carrier substrate by a patterning process. The separating the microelectrode from the carrier substrate includes: separating the microelectrode and the lead from the carrier substrate to transfer the microelectrode and the lead onto the first substrate.

In some embodiments, the at least one microelectrode includes a plurality of microelectrodes, the at least one lead includes a plurality of leads, and each microelectrode is connected to a corresponding one of the leads.

In some embodiments, the lead has a thickness of 10 μm to 50 μm and a width of 20 μm to 100 μm.

In some embodiments, after separating the microelectrode from the carrier substrate to transfer the microelectrode onto the first substrate, the method further includes: forming a second substrate on a side of the first substrate, which is provided with the microelectrode, wherein a through hole for the microelectrode to pass through is formed on the second substrate.

In some embodiments, the forming at least one recess on the carrier substrate includes: forming, on the carrier substrate, a plurality of recesses arranged in an array.

In some embodiments, the microelectrode is hemispherical.

DETAILED DESCRIPTION

To make those skilled in the art better understand the technical solutions of the present disclosure, a method for manufacturing a microelectrode film according to the present disclosure will be further described in detail below in conjunction with the accompanying drawings and specific embodiments.

Figure 1A:
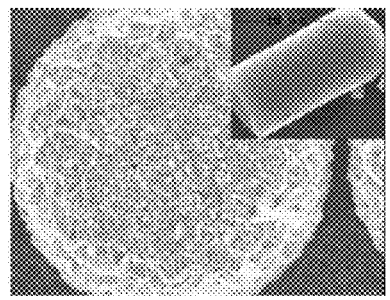
FIG. 1a is a schematic diagram of a cylindrical boron-doped diamond electrode.
Figure 1B:
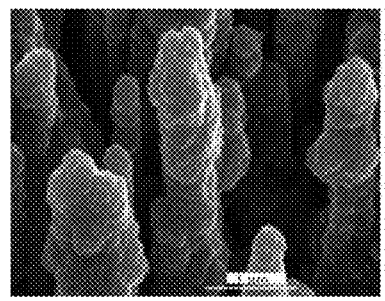
FIG. 1b is a schematic diagram of a nano grass-shaped boron-doped diamond electrode.

Referring to FIGS. 1a and 1b, the existing microelectrodes have shapes of needle, cylindrical, nano-grass, and porous, but the manufacturing process for forming these microelectrodes are different, in other words, the manufacturing processes for forming the exiting microelectrodes with various shapes are complicated.

Figure 2A:
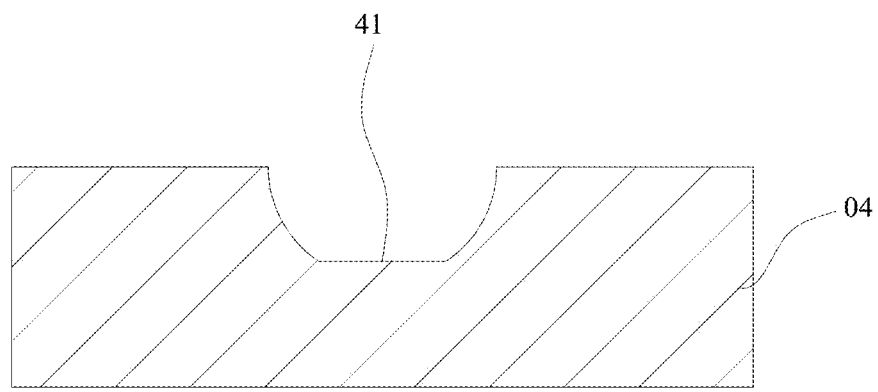
FIG. 2a is a schematic diagram showing a structure of a first recess in an embodiment of a method for manufacturing a microelectrode film according to the present disclosure.
Figure 2B:
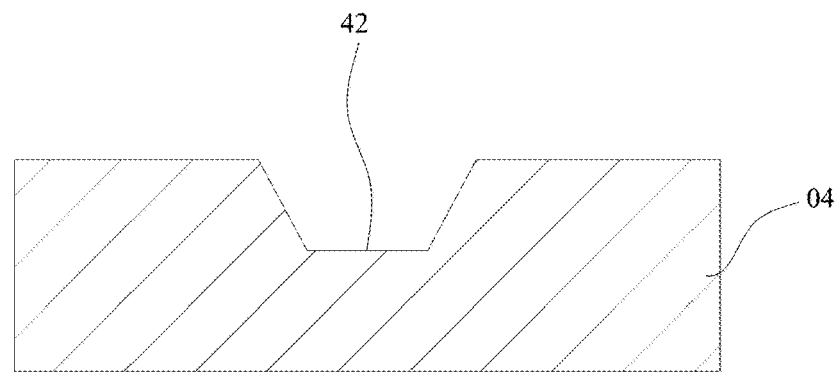
FIG. 2b is a schematic diagram showing a structure of a second recess in an embodiment of a method for manufacturing a microelectrode film according to the present disclosure.
Figure 2C:
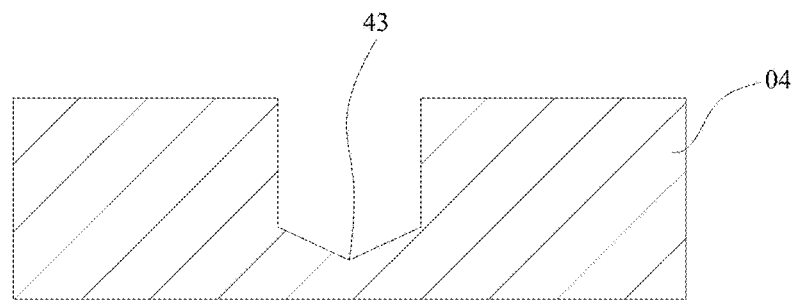
FIG. 2c is a schematic diagram showing a structure of a third recess in an embodiment of a method for manufacturing a microelectrode film according to the present disclosure.
Figure 3A:
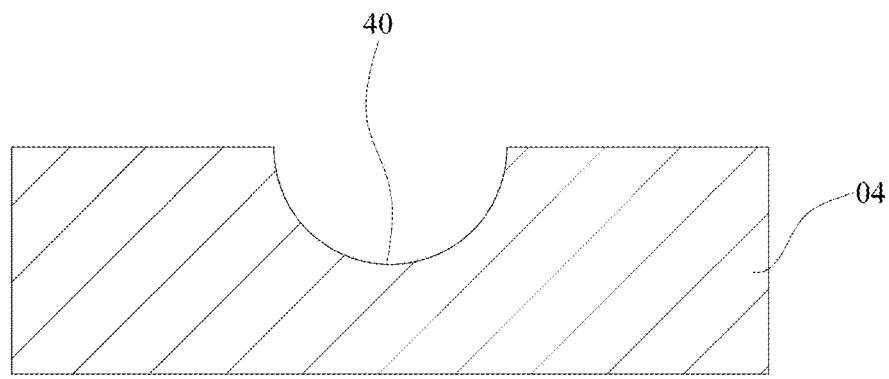
FIG. 3a is a schematic diagram of a microelectrode film formed after step 11 of an embodiment of a method for manufacturing a microelectrode film according to the present disclosure.
Figure 3B:
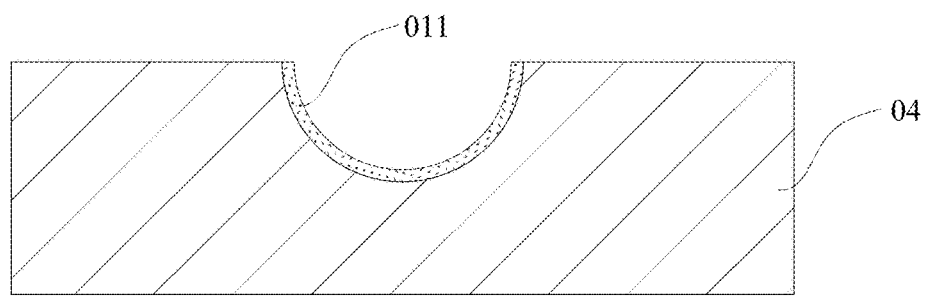
FIG. 3b is a schematic diagram of a microelectrode film formed after step 12 of an embodiment of a method for manufacturing a microelectrode film according to the present disclosure.
Figure 3C:
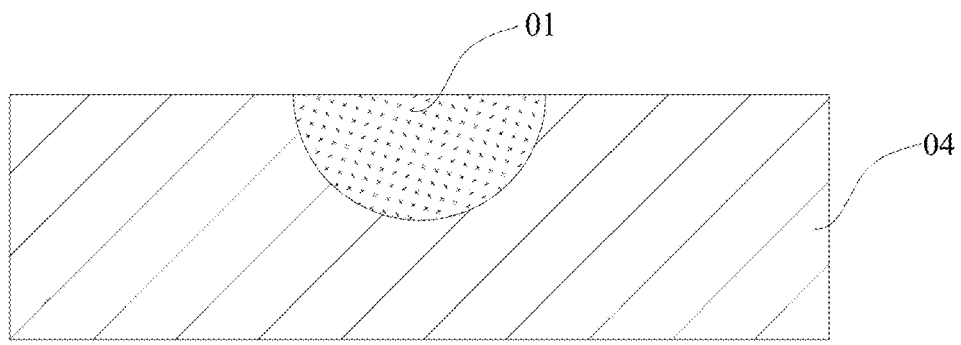
FIG. 3c is a schematic diagram of a microelectrode film formed after step 13 of an embodiment of a method for manufacturing a microelectrode film according to the present disclosure.
Figure 3D:
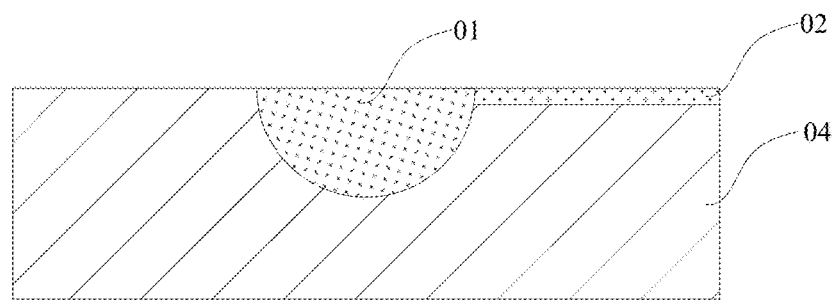
FIG. 3d is a schematic diagram of a microelectrode film formed after step 13a of an embodiment of a method for manufacturing a microelectrode film according to the present disclosure.
Figure 3E:
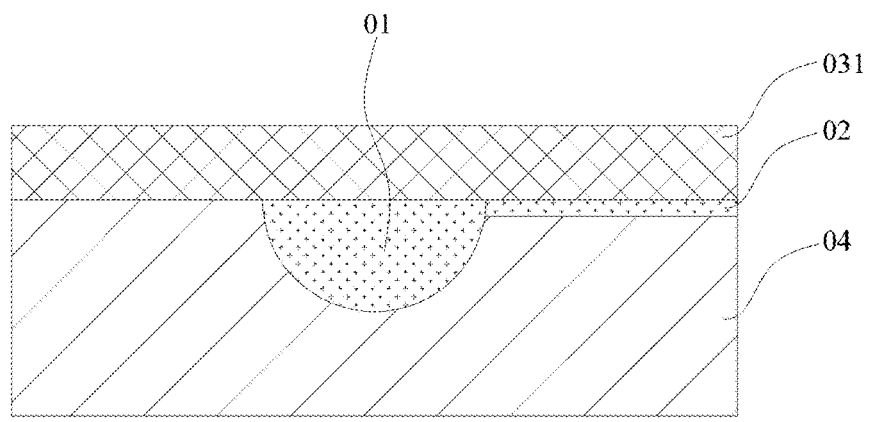
FIG. 3e is a schematic diagram of a microelectrode film formed after step 14 of an embodiment of a method for manufacturing a microelectrode film according to the present disclosure.
Figure 3F:
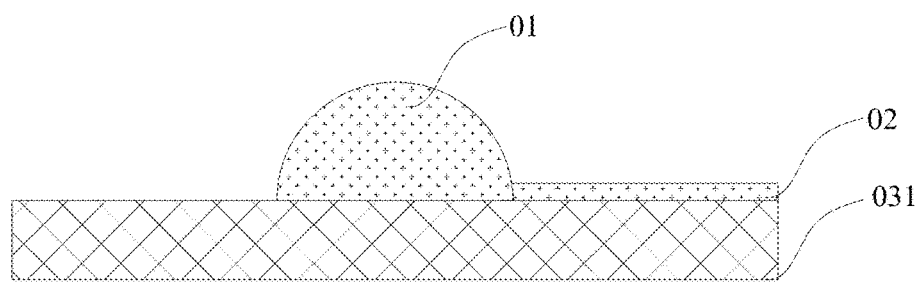
FIG. 3f is a schematic diagram of a microelectrode film formed after step 15 of an embodiment of a method for manufacturing a microelectrode film according to the present disclosure.
Figure 3G:
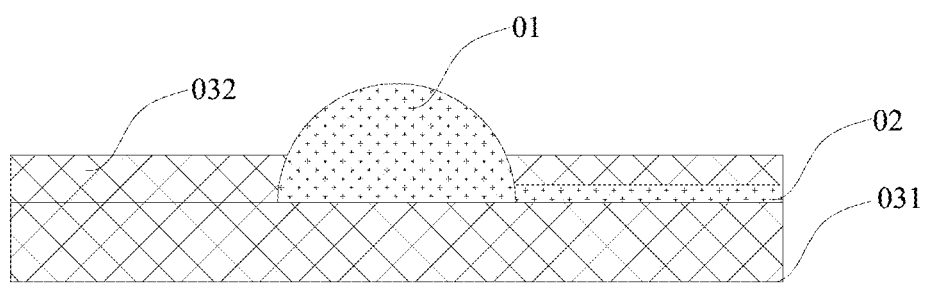
FIG. 3g is a schematic diagram of a microelectrode film formed after step 16 of an embodiment of a method for manufacturing a microelectrode film according to the present disclosure.
Figure 4:
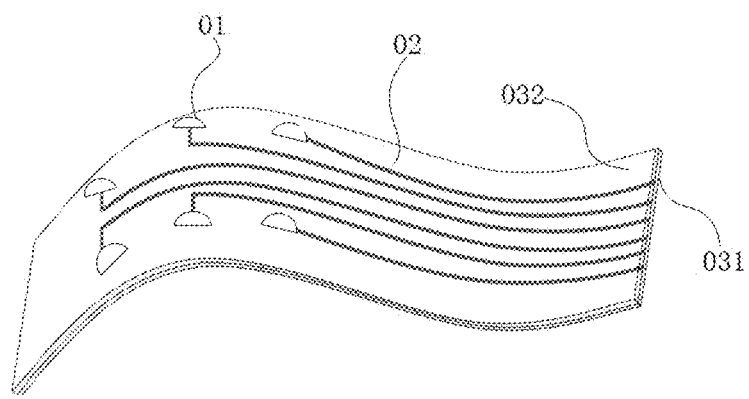
FIG. 4 is a schematic diagram of a microelectrode film according to an embodiment of a method for manufacturing a microelectrode film according to the present disclosure.
Figure 5:
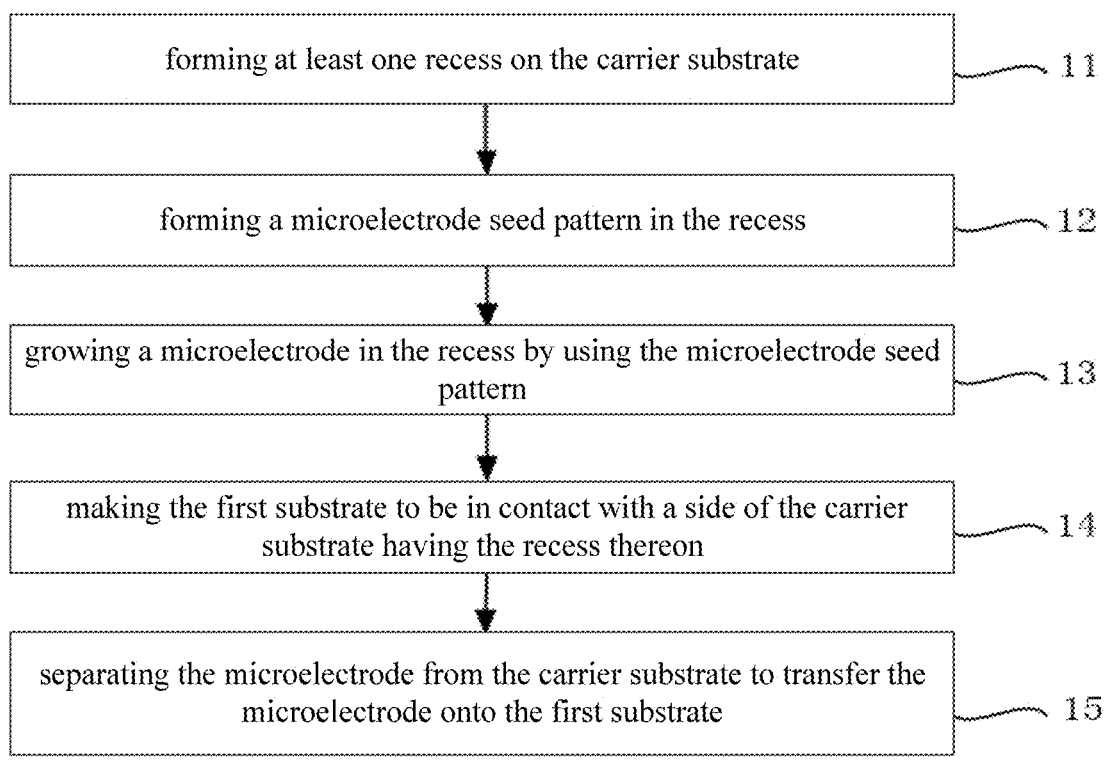
FIG. 5 is a flow chart of an embodiment of a method for manufacturing a microelectrode film according to the present disclosure.

Referring to FIGS. 1 to 6, the embodiments of the present disclosure provide a method for manufacturing a microelectrode film, and product forms of the microelectrode film manufactured by the method may refer to FIGS. 3f, 3g and 4. Referring to FIG. 5, the method may include steps 11 to 15.

In step 11, at least one recess 40 is formed on the carrier substrate 04, referring to FIG. 3a.

In this step, a patterning process may be adopted to form the recess 40 on the carrier substrate 04, and the shape, number, etc. of the recess 40 and corresponding process parameters may be set as needed.

In step 12, a microelectrode seed pattern 011 is formed in the recess 40, referring to FIG. 3b.

In step 13, a microelectrode 01 is grown in the recess 40 by using the microelectrode seed pattern 011, referring to FIG. 3c.

In this step, the microelectrode seed pattern 011 is grown in the recess 40, so that the shape of the microelectrode 01 as formed is the same as that of the recess 40, i.e., the shape of the recess 40 defines the shape of the microelectrode 01.

In step 14, the first substrate 031 is brought into contact with a side of the carrier substrate 04 having the recess 40 thereon, referring to FIG. 3e.

In this step, the first substrate 031 may be formed on the side of the carrier substrate 04 having the recess 40 thereon by coating, so that the microelectrode 01 is in contact with and connected to the first substrate 031 at the surface of the carrier substrate 04 having the recess 40 thereon.

In step 15, the microelectrode 01 is separated from the carrier substrate 04 to transfer the microelectrode 01 onto the first substrate 031, referring to FIG. 3f.

In the above scheme, the shape of the recess 40 defines the shape of the microelectrode 01. In principle, the microelectrode 01 having an arbitrary shape can be obtained if a recess 40 having a corresponding shape can be formed on the carrier substrate 04, and meanwhile, the forming of the recess 40 with various shapes on the carrier substrate 04 is easier to implement, for example, by adopting a patterning process, so that the microelectrode 01 with a required shape can be prepared by the method for manufacturing the microelectrode film with the above scheme according to actual needs, thereby improving the accuracy of a detection result of biological detection and enhancing the effect of biological stimulation.

In some embodiments, the carrier substrate 04 is a silicon substrate. In some embodiments, the microelectrode seed pattern 011 includes boron-doped diamond. In some embodiments, the first substrate 031 is a flexible substrate, for example, the first substrate 031 includes polyimide.

As a biological electrode, the boron-doped diamond (BDD) has good biocompatibility and electrochemical stability, and can operate for a long time in the biological environment with no deterioration of its conductivity. Meanwhile, the boron-doped diamond (BDD) electrode has the advantages of wide potential window, low background current, high signal-to-noise ratio and the like, and is an ideal material for biological detection and stimulation electrodes.

It is apt to form the recess 40 on a silicon substrate, and the silicon material is suitable for the growth of the boron-doped diamond, because it does not affect the growth of the boron-doped diamond seed, and it is easy to separate the grown microelectrode 01 from the silicon substrate.

Since polyimide is a polymer material having flexibility, when the microelectrode film needs to be attached to an organism, the first substrate 031 can be bent or curved according to the shape of the organism without damaging the organism.

Figure 6:
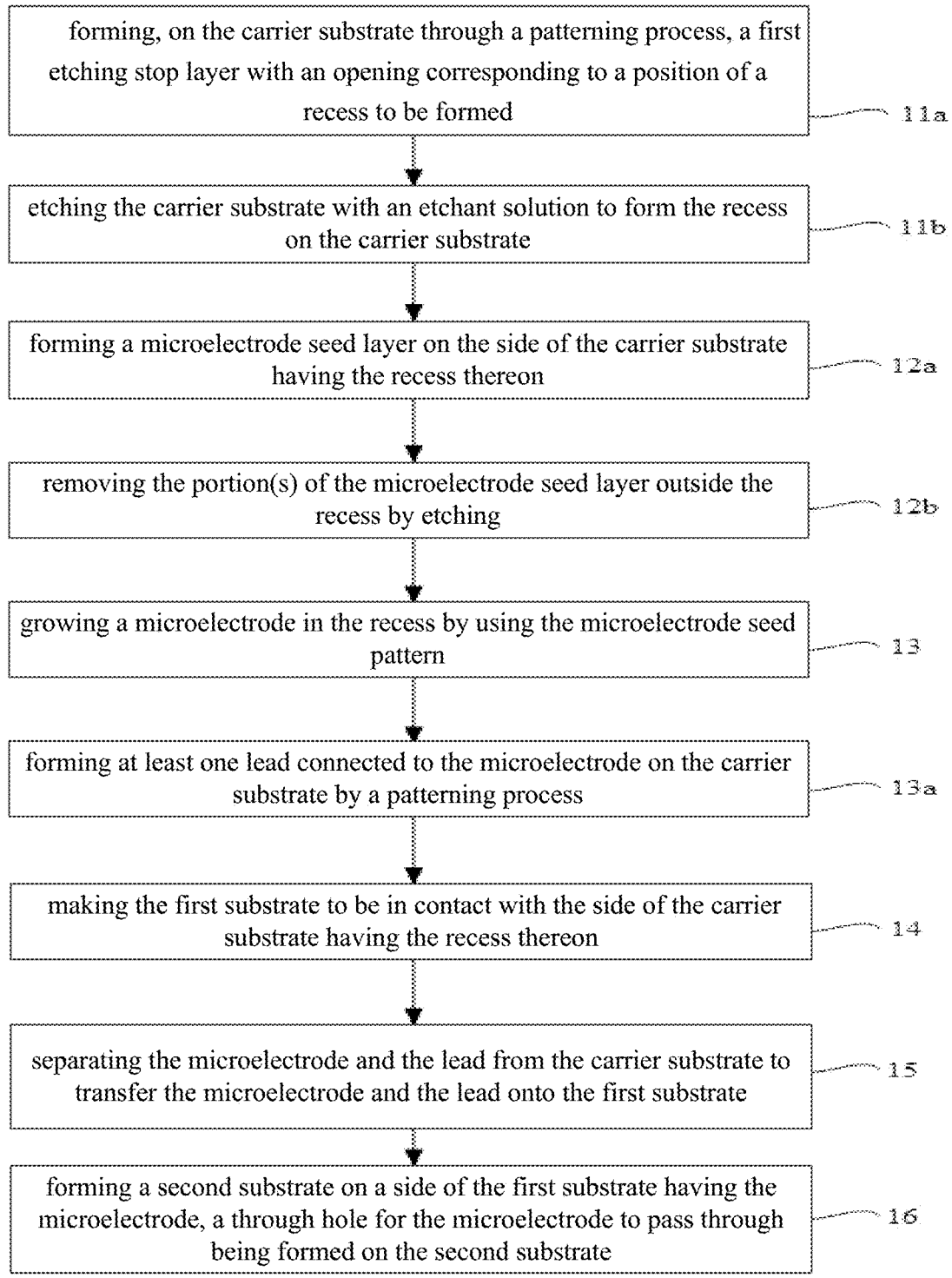
FIG. 6 is another flow chart of an embodiment of a method for manufacturing a microelectrode film according to the present disclosure.

In some embodiments, step 11 of FIG. 5 may include steps 11a and 11b of FIG. 6.

In step 11a, a first etching stop layer with an opening exposing a portion of the carrier substrate is formed on the carrier substrate 04 through a patterning process. For example, the exposed portion of the carrier substrate corresponds to a position where the recess 40 is to be formed.

In this step, a photoresist layer is coated on the carrier substrate, and the photoresist layer is subjected to photolithography to form an opening (through hole) on the photoresist layer, that is, a first etching stop layer is obtained, and the opening on the first etching stop layer is configured to define the shape of the opening of the recess 40.

In step 11b, the portion of the carrier substrate 04 exposed by the opening is etched with an etchant solution to form a recess 40 on the carrier substrate 04.

The step 11b may include isotropically etching the carrier substrate 04 with an etchant solution.

The isotropic etching means that the carrier substrate 04 is etched with the same etching effect in each direction, so that the side wall of the recess 40 formed on the etched carrier substrate 04 is arc-shaped (for example, the recess 40 is hemispherical), as shown in FIGS. 2a and 3a, and thus the surface of the microelectrode 01 formed in the recess 40 is also arc-shaped (for example, the microelectrode 01 is hemispherical), and thus the microelectrode 01 can be attached to an organism in a very friendly manner.

In some embodiments, isotropically etching the carrier substrate 04 includes: placing the carrier substrate 04 in the isotropic etchant solution, and stirring the isotropic etchant solution.

By stirring the etchant solution during the etching of the carrier substrate 04, the components of the etchant solution can be distributed more uniformly, so that after the carrier substrate 04 is etched, the shape of the side wall of the recess 40 formed on the carrier substrate 04 can be seen in FIG. 3a, and meanwhile, the opening of the recess 40 in FIG. 3a is circular, so that the recess 40 in FIG. 3a has a structure of partial sphere (a part of a whole sphere), and therefore, the microelectrode 01 formed in the recess 40 in FIG. 3a also has a structure of partial sphere, and the curvatures of the surface of the microelectrode are the same, thereby avoiding the concentration of charges, and reducing the risk of sharp-corner discharge.

Also, compared with acicular, cylindrical, nanometer grass, or porous microelectrode 01, the microelectrode 01 with the structure of partial sphere is in contact with the organism in a closer manner, that is, the effective area of microelectrode 01 in contact with the organism is larger, and the risk of injury to the organism due to the contact and friction of the microelectrode 01 with the organism is reduced, thereby improving the detection and stimulation performance of the microelectrode 01 on the organism.

In some embodiments, isotropically etching the carrier substrate 04 may include: placing the carrier substrate 04 in the isotropic etchant solution, and not stirring the isotropic etchant solution during the etching process of the carrier substrate 04, so that a first recess 41 is formed on the carrier substrate 04, and the shape of the first recess is shown in FIG. 2a.

It should be noted that, if a recess with another shape is required to be formed on the carrier substrate 04, other etching method, such as anisotropic etching, may also be performed on the carrier substrate 04. For example, the carrier substrate 04 is placed in an anisotropic etchant solution, and during the etching of the carrier substrate 04, the anisotropic etching solution is stirred, so that a second recess 42 is formed on the carrier substrate 04, and the shape thereof is as shown in FIG. 2b. For another example, the carrier substrate 04 is placed in the anisotropic etchant solution, and during the etching of the carrier substrate 04, the anisotropic etchant solution is not stirred, so that a third recess 43 is formed on the carrier substrate 04, and the shape thereof is as shown in FIG. 2c.

In some embodiments, step 12 of FIG. 5 may include steps 12a and 12b of FIG. 6.

In step 12a, a microelectrode seed layer is formed on the side of the carrier substrate 04 having the recess 40.

In step 12b, the portion(s) of the microelectrode seed layer outside the recess 40 is removed by etching.

Step 12b may be performed as follows: a second etching stop layer is formed on the microelectrode seed layer, and a photolithography process may be used to cover the second etching stop layer only on the microelectrode seed layer in each recess 40, and then, the portion(s) of the microelectrode seed layer not covered by the second etching stop layer, that is, the portion(s) outside the recess 40, is etched away. The second etching stop layer may be an aluminum mask, or may be a barrier material layer made of other materials and capable of blocking the etchant solution of the microelectrode seed layer. This step 12b may be followed by a step of etching away the second etching stop layer in each recess 40.

In some embodiments, referring to FIG. 6, after step 13 and before step 14 of FIG. 5, the manufacturing method further includes: step 13a, forming at least one lead 02 connected to the microelectrode 01 on the carrier substrate 04 by a patterning process, referring to FIG. 3d.

At this time, referring to FIG. 6, the above step 15 includes separating the lead 02 from the carrier substrate 04 to transfer the lead 02 onto the first substrate 031, referring to FIG. 3f.

In this embodiment, the lead 02 may be made of the same material as the microelectrode 01. The process for manufacturing the lead 02 may include: forming, on the carrier substrate 04 through a patterning process, a third etching stop layer with at least one through hole, the through hole of the third etching stop layer corresponding to a position where the lead 02 is to be formed; and forming a lead seed in the through hole of the third etching stop, and growing the lead 02 in the through hole of the third etching stop with the lead seed.

After the formation of the microelectrode 01 and the lead 02, the microelectrode 01 and the lead 02 should be transferred together onto the first substrate 031.

In some embodiments, in order to allow different electrical signals to be input in parallel through different microelectrodes 01, each microelectrode 01 is connected to a corresponding lead 02.

In some embodiments, the thickness of the lead is 10 μm to 50 μm, and the width of the lead is 20 μm to 100 μm.

Taking the microelectrode 01 in FIG. 4 as an example, the diameter thereof may be 10 μm to 200 μm. In some embodiments, the width of the lead 02 is not greater than the diameter of the microelectrode 01. The lead 02 in the above range has certain strength, so the lead 02 is not easy to be damaged, and meanwhile, the lead 02 in the above range has certain toughness, so the lead 02 can be bent and is not easy to be damaged.

In some embodiments, referring to FIG. 6, after step 15, the method further includes step 16, in which a second substrate 032 is formed on a side of the first substrate 031 having the microelectrodes 01, and a through hole for the microelectrode 01 to pass through is formed on the second substrate 032, the first substrate 031 and the second substrate 032 being attached together, referring to FIGS. 3g and 4.

In this step, the lead 02 is sandwiched between the first substrate 031 and the second substrate 032, so that the first substrate 031 and the second substrate 032 can keep the position of the lead unchanged when the microelectrode film is bent and curled.

In some embodiments, step 11 includes forming a plurality of recesses 40 arranged in an array on the carrier substrate 04.

In this embodiment, a plurality of recess 40 arranged in an array are formed on the carrier substrate 04, and a plurality of microelectrodes 01 arranged in an array can be arranged on the first substrate 031 obtained in the subsequent steps, as shown in FIG. 4, so that the microelectrode film has a faster response speed, higher sensitivity and higher current density, and can effectively solve the problem of small current of a miniaturized single microelectrode.

It should be noted that, in this description, relational terms such as first and second, and the like are used solely to distinguish one entity or action from another entity or action without necessarily requiring or implying any actual relationship or order between such entities or actions. Also, the terms "includes," "comprise" or any other variation thereof, are intended to cover a non-exclusive inclusion, such that a process, method, object, or apparatus that includes a list of elements does not include only those elements but may include other elements not expressly listed or elements inherent to such process, method, object, or apparatus. Without further limitation, an element defined by the phrase "including an . . . " does not exclude the presence of other identical elements in the process, method, object, or apparatus that includes the element.

Embodiments according to the present disclosure are as set forth above, and these embodiments are not intended to be exhaustive or to limit the disclosure to the precise embodiments described. Obviously, many modifications and variations are possible in light of the above teaching. The embodiments were chosen and described in order to best explain the principles and applications of the present disclosure, to thereby enable those skilled in the art to best utilize the present disclosure and make modification on the basis of the present disclosure. The present disclosure is to be limited only by the claims and their full scope and equivalents.

What is claimed is:

1. A method for manufacturing a microelectrode film, comprising:
   forming at least one recess on a carrier substrate by isotropic etching;
   forming a microelectrode seed pattern in the recess;
   growing a microelectrode in the recess by using the microelectrode seed pattern;
   making a first substrate to be in contact with a side of the carrier substrate having the recess thereon; and
   separating the microelectrode from the carrier substrate to transfer the microelectrode onto the first substrate,
   wherein the microelectrode is hemispherical.

2. The method of claim 1, wherein the microelectrode seed pattern comprises boron-doped diamond, and the first substrate is a flexible substrate.

3. The method of claim 1, wherein the forming at least one recess on the carrier substrate by isotropic etching comprises:
   forming, on the carrier substrate, a first etching stop layer with an opening by a patterning process, the opening exposing a portion of the carrier substrate; and
   isotopically etching the portion of the carrier substrate exposed by the opening by using an etchant solution to form the recess on the carrier substrate.

4. The method of claim 3, wherein the isotropically etching the portion of the carrier substrate exposed by the opening by using the etchant solution comprises:
   placing the carrier substrate in the etchant solution, and stirring the etchant solution.

5. The method of claim 1, wherein the carrier substrate is a silicon substrate.

6. The method of claim 3, wherein the opening is circular.

7. The method of claim 1, wherein the forming the microelectrode seed pattern in the recess comprises:
   forming a microelectrode seed layer on the side of the carrier substrate having the recess thereon, and removing a portion of the microelectrode seed layer outside the recess by etching.

8. The method of claim 1, wherein after growing the microelectrode in the recess by using the microelectrode seed pattern and before making the first substrate to be in contact with the side of the carrier substrate having the recess thereon, the method further comprises:
   forming at least one lead connected with the microelectrode on the carrier substrate by a patterning process, and
   the separating the microelectrode from the carrier substrate comprises:
   separating the microelectrode and the lead from the carrier substrate to transfer the microelectrode and the lead onto the first substrate.

9. The method of claim 8, wherein the at least one microelectrode comprises a plurality of microelectrodes, the at least one lead comprises a plurality of leads, and each of the plurality of microelectrode is connected to a corresponding one of the plurality of leads.

10. The method of claim 8, wherein the lead has a thickness of 10 µm to 50 µm and a width of 20 µm to 100 µm.

11. The method of claim 1, wherein after separating the microelectrode from the carrier substrate to transfer the microelectrode onto the first substrate, the method further comprises:
   forming a second substrate on a side of the first substrate, which is provided with the microelectrode, wherein a through hole for the microelectrode to pass through is formed on the second substrate.

12. The method of claim 1, wherein the forming at least one recess on the carrier substrate comprises:
   forming, on the carrier substrate, a plurality of recesses arranged in an array.

13. The method of claim 2, wherein the carrier substrate is a silicon substrate.

14. The method of claim 3, wherein the carrier substrate is a silicon substrate.

* * * * *